(12) United States Patent
Takahashi et al.

(10) Patent No.: US 7,148,387 B2
(45) Date of Patent: Dec. 12, 2006

(54) PROCESS FOR PRODUCING HYDROXYL GROUP-CONTAINING COMPOUND

(75) Inventors: Kenta Takahashi, Sodegaura (JP); Yutaka Ikushima, Sendai (JP)

(73) Assignees: Mitsui Chemicals, Inc., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 202 days.

(21) Appl. No.: 10/854,179

(22) Filed: May 27, 2004

(65) Prior Publication Data

US 2004/0242940 A1 Dec. 2, 2004

(30) Foreign Application Priority Data

May 28, 2003 (JP) .................................. 2003-150439

(51) Int. Cl.
*C07C 29/04* (2006.01)
*C07C 29/03* (2006.01)

(52) U.S. Cl. .................. 568/895; 568/896; 568/897; 568/898; 568/899; 568/900; 568/901

(58) Field of Classification Search ............... 568/895, 568/896, 897, 898, 899, 900, 901
See application file for complete search history.

(56) References Cited

U.S. PATENT DOCUMENTS 4,150,245 A  4/1979  Sommer et al.

FOREIGN PATENT DOCUMENTS

| | | | |
|---|---|---|---|
| EP | 1 386 195 | A | 3/1975 |
| EP | 1 564 223 | A | 4/1980 |
| JP | 47-30608 | A | 11/1972 |
| JP | 47-31908 | A | 11/1972 |
| JP | 47-31909 | A | 11/1972 |
| JP | 49-117412 | A | 11/1974 |
| JP | 49-126607 | A | 12/1974 |
| JP | 49-126609 | A | 12/1974 |
| JP | 51-44915 | B | 12/1976 |
| JP | 52-113904 | A | 9/1977 |
| JP | 52-133095 | A | 11/1977 |
| JP | 52-133910 | A | 11/1977 |
| JP | 53-84906 | A | 7/1978 |
| JP | 63-218251 | A | 9/1988 |
| JP | 8-143493 | A3 | 6/1996 |
| JP | 8-151339 | A3 | 6/1996 |
| JP | 11-76836 | A | 3/1999 |
| JP | 2003-34657 | A | 2/2003 |

*Primary Examiner*—Elvis O. Price
(74) *Attorney, Agent, or Firm*—Birch, Stewart, Kolasch & Birch, LLP

(57) ABSTRACT

Discloses a process for efficiently producing a hydroxyl group containing compound with a simple apparatus and simple procedures using a very small amount of a catalyst, which process reduces a catalyst recovering step and a catalyst neutralization step vastly and does not require catalyst regeneration and catalyst exchange.

The process for producing a hydroxyl group containing compound comprises allowing an aqueous solution containing 1 ppb to 500 ppm of an acid catalyst to react with an aliphatic double bond having compound in a molar ratio (water/aliphatic double bond having compound) of water to aliphatic double bond having compound of from 1 to 50, at a reaction temperature of from 200 to 600° C. under a reaction pressure of from 1 to 100 MPa and thereby conducting hydration reaction of the aliphatic double bond containing compound with water.

9 Claims, 2 Drawing Sheets

PROCESS FOR PRODUCING HYDROXYL GROUP-CONTAINING COMPOUND

This Non-provisional application claims priority under 35 U.S.C. § 119(a) on Patent Application No(s). 2003-150439 filed in Japan on May 28, 2003, the entire contents of which are hereby incorporated by reference.

FIELD OF THE INVENTION

The present invention relates to a process for producing a hydroxyl group-containing compound by hydration reaction of an aliphatic double bond having compound with water, and more particularly, it relates to a process for producing an alcohol with hydration of olefins.

BACKGROUND OF THE INVENTION

Alcohol production by hydration of olefins has conventionally been carried out by a process of using an acid catalyst such as sulfuric acid and the like. In the process of using sulfuric acid, an olefin is allowed to react with water in the presence of sulfuric acid to generate a sulfuric ester and then it hydrolyzes to generate a crude alcohol. A purified alcohol is prepared by separating an unreacted olefin, water and byproducts from the crude alcohol with rectification or other methods. In the production method, sulfuric acid necessary for the production of the sulfuric ester is in an amount equimolar with olefin, namely in terms of weight, of 70%. Therefore, because a large amount of sulfuric acid having high corrosive properties is present inside a reactor, this process has serious problems such that troubles caused by corrosion of materials in each place are easily induced in the equipment preservation aspect and an operator has a danger of receiving sulfuric acid spurted in the safety aspect.

After the hydrolysis, the separated aqueous sulfuric acid solution is again concentrated into an aqueous solution of high concentration and then submitted to recycling. The increase of the number of steps necessary for the recycling increases the cost of plant construction and the cost of heating necessary for the concentration so that the process is uneconomical. We must consider apparatus corrosion in not only reactors but also steps where sulfuric acid having a high concentration is passed through in the same manner so that the provision for corrosion results in an increase of the maintenance cost. The waste liquid containing sulfuric acid in a high concentration constantly exhausted is necessary to be neutralized with sodium hydroxide etc and a resultant sulfate is necessary to be treated as an industrial waste to increase the environmental load.

Under the circumstances, a gas phase reaction process of directly hydrating olefin and water with a phosphoric acid supported catalyst has been developed as referred to Patent literatures 1 to 3. In this process, from crude alcohol generated from the direct hydration, an unreacted olefin, water and byproducts are separated by rectification and other methods and thereby purified alcohol is prepared. This process has been industrially conducted in many cases because the steps are simplified as compared with the process of using sulfuric acid and this process has no danger of using a strong acid having a high concentration. However, in general, this process has a low conversion rate of olefin so that the production amount of alcohol per volume is very low and thereby a reactor becomes too large and also the energy required for recycle of an unreacted olefin becomes large. Further, there is a problem such that the catalyst capabilities of phosphoric acid used as a catalyst component are lowered by scattering thereof with the progress of the reaction and thereby the productivity is lowered.

As another process of the direct hydration, a process of using a water-soluble heteropolyacid as a catalyst has been developed as referred to Patent literatures 4 to 6.

In this process, an olefin and water are directly subjected to hydration in the presence of a heteropolyacid to generate crude alcohol. From the crude alcohol, unreacted olefins, heteropolyacid, water and byproducts are separated by rectification and other methods and thereby purified alcohol is prepared. Because heteropolyacid has low corrosive properties, the maintenance cost for apparatus is improved, but the concentration of heteropolyacid in the reaction steps is several thousands ppm per the flow rate of a reaction liquid and it is none too low, to make the economical properties worse. Further, no small amount of heteropolyacid is constantly discharged and thereby neutralization treatment is necessary. Similar to the sulfuric acid process, the heteropolyacid waste liquid constantly discharged is necessary to be subjected to neutralization treatment and a salt of heteropolyacid generated after the neutralization treatment is necessary to be treated as an industrial waste to increase the environmental load. Meanwhile, because heteropolyacid is expensive, it is considered that heteropolyacid is separated from the waste liquid and submitted to reuse. In this case, the cost for the separation, such as ion exchange resin treatment step and the like is large to increase the production cost. Additionally, the molar ratio of water to olefin in the raw materials is 27 and it is higher as compared with other prior techniques so that the production efficiency is lowered.

Processes of using such a soluble catalyst other than the heteropolyacid have been developed. For example, there are a process of using trifluoromethane sulfonic acid (as referred to Patent literature 7) and a process of using a titanium sulfate aqueous solution (as referred to Patent literature 8).

In any processes, however, the catalyst in a reactor inevitably has a high concentration in order to promote the reaction and thereby the production cost is increased. Further, the post treatment steps after the use of the catalyst are increased so that the plant cost is also increased in the processes.

As another direct hydration process, a process of using a strong acid ion exchange resin catalyst is also developed as referred to Patent literatures 9 to 11. In this process, an olefin and water are directly subjected to hydration reaction in a reactor filled with a solid catalyst to generate crude alcohol. From the crude alcohol, an unreacted olefin, water and byproducts are separated by rectification and other methods and thereby purified alcohol is produced. When the process of using the soluble catalyst such as sulfuric acid or heteropolyacid is employed, it is necessary to employ a step of recovering the catalyst. However, using the solid catalyst, it is unnecessary to employ the step of recovering the catalyst and also unnecessary to employ neutralization treatment of acid components contained in a waste liquid. But, in the process of using the solid catalyst, the catalyst is deteriorated with time and it is necessary to increase the temperature or decrease the production in order to keep a space time yield. For these reasons, the operation control is complicated to affect a bad influence on economic properties simultaneously. Further, the deteriorated catalyst has to be regenerated to deteriorate the economic properties in this stage. When the catalyst cannot be regenerated, exchange operation is required and thereby the catalyst exchange requires considerable several days to lower the production. Furthermore, large amounts of catalyst wastes generated are inevitably treated as an industrial waste.

In addition to the above processes, many processes of using a solid acid catalyst have been developed. For example, a process of using ZSM-5 zeolite as a catalyst is disclosed as referred to Patent literature 12. Furthermore, as a process of improving the lifetime of the solid acid catalyst or improving the capabilities thereof, some processes are disclosed as referred to Patent literatures 13 to 15. However, in any processes, the deterioration of the solid acid catalyst with time is inevitable and the fundamental improvement for the processes is necessary.

As described above, on present showing, these conventional processes have inevitable problems including economical deterioration caused by various reasons, industrial waste treatment and the like.

Previously, the present inventors invented a direct hydration process without need of an acid catalyst in the production of alcohols by hydration reaction of an olefin and water as referred to Patent literature 16. This process utilizes an acid catalyst function, which is expressed near the critical point of water.

Utilizing the technique, we have studied earnestly in order to further improve the productivity. Thus, the present invention has been accomplished.

Patent literature 1: JP-B-51(1976)-44915
Patent literature 2: JP-A-52(1977)-133095
Patent literature 3: JP-A-53(1978)-84906
Patent literature 4: JP-A-47(1972)-30608
Patent literature 5: JP-A-47(1972)-31908
Patent literature 6: JP-A-47(1972)-31909
Patent literature 7: JP-A-52(1977)-133910
Patent literature 8: JP-A-52(1977)-113904
Patent literature 9: JP-A-49(1974)-117412
Patent literature 10: JP-A-49(1974)-126607
Patent literature 11: JP-A-49(1974)-126609
Patent literature 12: JP-A-63(1988)-218251
Patent literature 13: JP-A-8(1996)-143493
Patent literature 14: JP-A-8(1996)-151339
Patent literature 15: JP-A-11(1999)-76836
Patent literature 16: JP-A-2003-34657

OBJECT OF THE INVENTION

It is an object of the invention to provide a process for producing a hydroxyl group-containing compound by hydration reaction of an aliphatic double bond having compound with water, and more particularly, to provide a process for producing a hydroxyl group-containing compound efficiently by using a simple apparatus through simple procedures with a very small amount of a catalyst, which process can vastly reduce the step of recovering the catalyst and the catalyst neutralization step and does not require catalyst regeneration, catalyst exchange and the like.

SUMMARY OF THE INVENTION

The present invention is a process for producing a hydroxyl group-containing compound as described below.

(1) The process for producing a hydroxyl group containing compound which process comprises allowing an acid catalyst containing aqueous solution having an acid catalyst concentration of 1 ppb to 500 ppm to react with an aliphatic double bond having compound in a molar ratio (water/aliphatic double bond having compound) of water to aliphatic double bond having compound of from 1 to 50, at a reaction temperature of from 200 to 600° C. under a reaction pressure of from 1 to 100 MPa and thereby conducting hydration reaction of the aliphatic double bond containing compound with water.

(2) The process for producing a hydroxyl group-containing compound according to the claim (1) wherein the acid catalyst containing aqueous solution has an acid catalyst concentration of from 1 ppb to 300 ppm.

(3) The process for producing a hydroxyl group containing compound according to the claim (1) or (2) wherein the molar ratio (water/aliphatic double bond having compound) of water to the aliphatic double bond having compound is from 2 to 25.

(4) The process for producing a hydroxyl group-containing compound according to the claim (1) wherein the acid catalyst containing aqueous solution has an acid catalyst concentration of from 1 ppb to 70 ppm, and the molar ratio (water/aliphatic double bond having compound) of water to the aliphatic double bond having compound is from 2 to 25.

(5) The process for producing a hydroxyl group-containing compound according to any one of the claims (1) to (4) wherein the reaction temperature is from 250 to 450° C. and the reaction pressure is from 4 to 90 MPa.

(6) The process for producing a hydroxyl group-containing compound according to any one of the claims (1) to (5) wherein the acid catalyst is any one of hydrochloric acid, hydrogen chloride, chlorous acid, hypochlorous acid, sulfuric acid, sulfurous acid, nitric acid, nitrous acid, hydrogen fluoride, hydrofluoric acid, hydrogen bromide, hydrobromic acid, hydrogen iodide, hydriodic acid, orthophosphoric acid, metaphosphoric acid, phosphinic acid, phosphonic acid, diphosphoric acid, tripolyphosphoric acid, boric acid, silicotungstic acid, sodium silicotungstate, phosphotungstic acid, sodium phosphotungstate, silicomolybdic acid, sodium silicomolybdate, phosphomolybdic acid, sodium phosphomolybdate, benzoic acid, acetic acid, salicylic acid, oxalic acid, trifluoromethane sulfonic acid, p-toluenesulfonic acid and phenol.

(7) The process for producing a hydroxyl group-containing compound according to any one of the claims (1) to (6) wherein the acid catalyst is any one of hydrochloric acid, sulfuric acid, nitric acid, orthophosphoric acid and metaphosphoric acid.

(8) The process for producing a hydroxyl group-containing compound according to any one of the claims (1) to (7) wherein the aliphatic double bond having compound is a monoolefin or diolefin.

(9) The process for producing a hydroxyl group containing compound according to any one of the claims (1) to (7) wherein the aliphatic double bond having compound comprises at least one selected from ethylene, propylene, 1-butene, 2-butene, isobutene, 1-pentene, 2-pentene, isopentene, 1-hexene, 2-hexene, 3-hexene, isohexene, heptene, octene, nonene, decene, dodecene, cyclohexene, 1,3-butadiene, 1,3-pentadiene, 1,4-pentadiene, 1,3-hexadiene, 1,4-hexadiene, 1,5-hexadiene, 2,4-hexadiene, 1,6-heptadiene, 1,7-octadiene, 1,8-nonadiene, 1,9-decadiene, 1,3-cyclohexadiene, 1,4-cyclohexadiene, styrene, allyl benzene, trans-stilbene, cis-stilbene, triphenylethene, tetraphenyl ethene and divinyl benzene.

DETAILED DESCRIPTION OF THE INVENTION

The process for producing the hydroxyl group-containing compound according to the present invention will be described in detail below.

In the present invention, an aliphatic double bond having compound and water are subjected to hydration reaction in the presence of an acid catalyst to produce a hydroxyl group-containing compound.

(Aliphatic double bond having compound)

The aliphatic double bond having compound used in the invention is a compound having at least one aliphatic group carbon-carbon double bond capable of hydrating, such as a monoolefin, a diolefin and the like as described below.

Examples of the monoolefin may include aliphatic monoolefins and aromatic group-containing monoolefins represented by the following formula (1):

$$R^1R^2C=CR^3R^4 \quad (1)$$

In the formula, each of $R^1$ to $R^4$ is independently a saturated aliphatic group, aromatic group or hydrogen.

Specific examples of the aliphatic monoolefins may include ethylene, propylene, 1-butene, 2-butene, isobutene, 1-pentene, 2-pentene, isopentene, 1-hexene, 2-hexene, 3-hexene, isohexene, heptene, octene, nonene, decene, dodecene and cyclohexene. Specific examples of the aromatic group-containing monoolefins may include styrene, allylbenzene, trans-stilbene, cis-stilbene, triphenylethene and tetraphenylethene.

Examples of the diolefin may include aliphatic diolefins and aromatic group containing diolefins represented by the following formula (2):

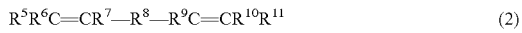

$$R^5R^6C=CR^7-R^8-R^9C=CR^{10}R^{11} \quad (2)$$

In the formula, each of $R^5$ to $R^7$ and each of $R^9$ to $R^{11}$ are independently a saturated aliphatic group, aromatic group or hydrogen, and $R^8$ is a saturated aliphatic group, aromatic group or a single bond.

Specific examples of the aliphatic diolefins may include 1,3-butadiene, 1,3-pentadiene, 1,4-pentadiene, 1,3-hexadiene, 1,4-hexadiene, 1,5-hexadiene, 2,4-hexadiene, 1,6-heptadiene, 1,7-octadiene, 1,8-nonadiene, 1,9-decadiene, 1,3-cyclohexadiene and 1,4-cyclohexadiene. Specific examples of the aromatic group-containing diolefins may include divinylbenzene and the like.

(Acid catalyst)

Examples of the acid catalyst used in the invention may include hydrochloric acid, hydrogen chloride, chlorous acid, hypochlorous acid, sulfuric acid, sulfurous acid, nitric acid, nitrous acid, hydrogen fluoride, hydrofluoric acid, hydrogen bromide, hydrobromic acid, hydrogen iodide, hydriodic acid, orthophosphoric acid, metaphosphoric acid, phosphinic acid, phosphonic acid, diphosphoric acid, tripolyphosphoric acid, boric acid, silicotungstic acid, sodium silicotungstate, phosphotungstic acid, sodium phosphotungstate, silicomolybdic acid, sodium silicomolybdate, phosphomolybdic acid, sodium phosphomolybdate, benzoic acid, acetic acid, salicylic acid, oxalic acid, trifluoromethane sulfonic acid, p-toluenesulfonic acid and phenol, and preferably may include water-soluble acid catalyst such as hydrochloric acid, hydrogen chloride, chlorous acid, hypochlorous acid, sulfuric acid, sulfurous acid, nitric acid, nitrous acid, hydrogen fluoride, hydrofluoric acid, hydrogen bromide, hydrobromic acid, hydrogen iodide, hydriodic acid, orthophosphoric acid, metaphosphoric acid, phosphinic acid, phosphonic acid, diphosphoric acid, tripolyphosphoric acid, boric acid, silicotungstic acid, sodium silicotungstate, phosphotungstic acid, sodium phosphotungstate, silicomolybdic acid, sodium silicomolybdate, phosphomolybdic acid and sodium phosphomolybdate.

Among the above acid catalysts, hydrochloric acid, sulfuric acid, nitric acid, orthophosphoric acid and metaphosphoric acid are preferred.

In the process for producing the hydroxyl group containing compound according to the invention, the acid catalyst is used in such a proportion that the concentration of an acid catalyst containing aqueous solution submitted to reaction with the aliphatic double bond-having compound is generally from 1 ppb to 500 ppm, preferably 1 ppb to 300 ppm, more preferably 1 ppb to 70 ppm, especially 10 ppb to 50 ppm.

When the acid catalyst is used in the above proportion, the hydration reaction can be carried out at a sufficient rate, and the catalyst recovering step and the catalyst neutralizing step can be vastly reduced and further catalyst regeneration, catalyst exchange and the like are unnecessary.

(Reaction conditions)

The hydration reaction of the aliphatic double bond having compound with water is preferably carried out in the presence of the acid catalyst at a reaction temperature of from 200 to 600° C. under a reaction pressure of from 1 to 100 MPa, more preferably at a reaction temperature of from 250 to 450° C. under a reaction pressure of from 4 to 90 MPa, further preferably at a reaction temperature of from 250 to 450° C. under a reaction pressure of from 5.5 to 50 MPa, most preferably at a reaction temperature near the critical point under a reaction pressure near the critical point, namely at the supercritical or subcritical temperature under the supercritical or subcritical pressure. The critical point is a critical temperature and critical pressure at which a gas and a liquid can coexist and is determined by a molar ratio of water to the aliphatic double bond having compound (water/aliphatic double bond having compound). In the present invention, the supercritical or subcritical reaction temperature and supercritical or subcritical reaction pressure near the critical point are specifically from 270 to 400° C. and from 5.5 to 50 MPa, respectively.

When the temperature and the pressure are in the above ranges, the hydration reaction can be carried out at a sufficient rate.

The molar ratio of water to the aliphatic double bond having compound (water/aliphatic double bond having compound) is generally from 1 to 50, preferably 1 to 25, more preferably 2 to 20, especially 5 to 15.

When the molar ratio of water to the aliphatic double bond having compound is the above range, a problem induced in the low molar ratio such that the reactor size is increased owing to the prolonged reaction time is avoided, and a problem induced in the high molar ratio such that the amount of water used per production is increased to increase the reactor size or energy used for increasing the water pressure is avoided.

(Hydroxyl group-containing compound)

The hydroxyl group-containing compound produced in accordance with the process of the present invention is a compound in which any one of two carbon atoms constituting the double bond of the aliphatic double bond having compound is linked with a hydroxyl group. When the aliphatic double bond having compound is a monoolefin represented by the formula (1), alcohols represented by the following formulas are produced:

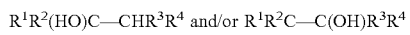

$$R^1R^2(HO)C-CHR^3R^4 \text{ and/or } R^1R^2C-C(OH)R^3R^4$$

The hydroxyl group-containing compound prepared preferably in accordance with the process of the invention may include ethanol, 2-propanol, 2-butanol, 2-methyl-2-propanol, 2-pentanol, 3-pentanol, 3-methyl-2-butanol, 2-methyl-2-butanol, 2-hexanol, 3-hexanol, 2-methyl-2-pentanol, 3-methyl-2-pentanol, 4-methyl-2-pentanol, 2-methyl-3-pentanol, 3-methyl-3-pentanol, 2-ethyl-2-butanol, 2,3-dimethyl-2-butanol, 3,3-dimethyl-2-butanol and 2,3-dimethyl-3-butanol The aliphatic double bond having compounds corresponding to these compounds may include ethylene, propylene, 1-butene, 2-butene, isobutene, 1-pentene, 2-pentene, 2-methyl-1-butene, 3-methyl-1-butene, 3-methyl-2-butene, 1-hexene, 2-hexene, 3-hexene, 2-methyl-1-pentene, 3-methyl-1-pentene, 4-methyl-1-pentene, 2-methyl-2-pentene, 3-methyl-2-pentene, 4-methyl-2-pentene, 2-ethyl-1-butene, 2,3-dimethyl-1-butene, 3,3-dimethyl-1-butene and 2,3-dimethyl-2-butene.

The present invention is preferably used for producing ethanol, 2-propanol, 2-butanol, 2-methyl-2-propanol, 2-pentanol, 2-hexanol and 4-methyl-2-pentanol.

(Illustration of Production)

The process for producing the hyroxyl group containing compound by hydration reaction of the aliphatic double bond having compound with water according to the invention will be described below with reference to the case where the aliphatic double bond having compound is a monoolefin.

The reaction may be carried out by any of the batch wise method and continuous method. The reaction with the continuous method will be described with reference to FIG. 1 showing one embodiment of a general flow sheet of the steps of carrying out the invention. Persons skilled in the art can easily conduct the process with the batch wise method by applying the description of the process with the continuous method.

From a raw material tank 1, water is fed to a tank 6 for preparing an acid catalyst containing aqueous solution through a line 4. The acid catalyst is fed from an acid catalyst tank 2 to the tank 6 for preparing the acid catalyst containing aqueous solution through a line 5 and mixed with water. The water used is preferably ion-exchange water. The acid catalyst containing aqueous solution prepared herein is fed to a reactor 9 through a line 7. Before feeding to the reactor, the acid catalyst containing aqueous solution may be optionally preheated and then fed to the reactor. An olefin is fed from a raw material tank 3 to the reactor 9 through a line 8. In this case, the olefin may be optionally preheated and then fed to the reactor. The generated reaction liquid is fed to a plant for a separating process 11 through a line 10 to separate an unreacted olefin and an acid catalyst containing aqueous solution. The unreacted olefin is recycled in the reactor 9 through a line 12. The acid catalyst containing aqueous solution is recycled to the reactor 9 through a line 13. Through a line 14, a crude alcohol containing a byproduct and the like is fed into a plant for a purifying process 15 and the byproduct and the like are separated by a method such as rectification, etc through a line 16. Thereafter, alcohol is produced through a line 17 and stored into a production tank 18.

In the reactor 9, the monoolefin and the acid catalyst containing aqueous solution having a acid catalyst concentration of 1 ppb to 500 ppm are allowed to contact each other in a molar ratio of water to the aliphatic double bond having compound (water/aliphatic double bond having compound) of from 1 to 50, at a high temperature of from 200 to 600° C. under a high pressure of 1 to 100 MPa. In this reaction, water is in any one state of gas, liquid and super critical states in accordance with the temperature and pressure. The reaction is carried out in preferable conditions such that the acid catalyst concentration is from 1 ppb to 300 ppm, preferably 1 ppb to 70 ppm, more preferably 10 ppb to 50 ppm, the reaction temperature is from 200 to 600° C. and the reaction pressure is from 1 to 100 MPa, more preferably 250 to 450° C. and 4 to 90 MPa, furthermore preferably 250 to 450° C. and 5.5 to 50 MPa. The hydration reaction is most preferably carried out at a reaction temperature near the critical point under a reaction pressure near the critical point, namely, at a supercritical or subcritical temperature under a supercritical or subcritical pressure.

The molar ratio of water to the aliphatic double bond having compound (water/aliphatic double bond having compound) is preferably from 1 to 25, more preferably 2 to 20 furthermore preferably 5 to 15.

The reaction time (residence time) in the reactor 9 is adequately determined according to the kind of the monoolefin, reaction temperature, reaction pressure and other conditions, and generally about from 0.1 sec to 30 min.

EFFECT OF THE INVENTION

According to the production process of the present invention, hydration reaction of an aliphatic double bond having compound with water can be carried out at a sufficient rate in the presence of a slight amount of an acid catalyst at a high temperature under a high pressure. More particularly, the process can vastly reduce the conventional step of recovering the catalyst and catalyst neutralization step and does not require catalyst regeneration, catalyst exchange and the like so that a hydroxyl group-containing compound can be prepared efficiently at a low cost.

EXAMPLE

The present invention will be described in more detail below with reference to the following examples, but it is not limited by the examples.

In each of Examples and Comparative Examples, hydration reaction of an olefin was carried out with the continuous method using a flow reaction apparatus as shown in FIG. 2. The reaction apparatus as shown in FIG. 2 has pumps 23, 24, a reactor 25, a heater 26 and a back pressure control valve 27. An acid catalyst containing aqueous solution prepared by mixing water as a raw material and an acid catalyst was fed to the reactor 25 from a tank 21 using the pump 23, a raw material olefin was fed to the reactor 25 from a tank 22 using the pump 24 and they were mixed in the reactor 25 to cause hydration reaction. The temperature and pressure of the reactor 25 were regulated by the heater 26 and the back pressure control valve 27 and a reaction liquid was taken out from a tank 28 for reaction liquid. The reaction time (residence time) was controlled by the flow rates of the raw material acid catalyst containing aqueous solution and the raw material olefin with controlling the pumps 23, 24.

In Examples and Comparative Examples, a space time yield (STY) was determined from the composition of a reaction liquid by the following formula (1). The composition of the reaction liquid was determined by the analysis with a gas chromatography mass spectrometer (GC-MS) manufactured by Agilent Technologies.

Formula (1):

| | |
|---|---|
| Styrene-isoprene-styrene block copolymer (D-KX401CS) | 23.0% |
| Polyisobutylene (Tetrax 6T) | 14.0% |
| Polyisobutylene (Vistanex MML-100) | 8.0% |
| Petroleum resin (Arkon P-100) | 15.0% |

-continued

| | |
|---|---|
| Liquid paraffin (Cristol J-352) | 24.0% |
| Glycol salicylate | 8.0% |
| L-menthol | 8.0% |

Example 1

Propylene was used as an olefin and the reactor 25 was heated with the heater 26. Hydration reaction was carried out by regulating the reactor 25 at a reaction temperature of 380° C. under a reaction pressure of 30 MPa and the sulfuric acid concentration of an acid catalyst containing aqueous solution of 50 ppm. The molar ratio of water to propylene was set to 10 and the residence time was set to 10 min by regulating the flow rate of the acid catalyst containing aqueous solution to 102 g/h, the propylene flow rate to 23.8 g/h and the volume of the reactor to 50 mL. In this reaction, the STY was 1,960 g/g-cat·h.

Example 2

The procedure of Example 1 was repeated except that the temperature was 370° C. and the molar ratio of water to propylene was set to 10 and the residence time was set to 10 min by regulating the flow rate of the acid catalyst containing aqueous solution to 109 g/h and the propylene flow rate to 25.3 g/h. In this reaction, the STY was 2,310 g/g-cat·h.

Example 3

The procedure of Example 1 was repeated except that the temperature was 360° C. and the molar ratio of water to propylene was set to 10 and the residence time was set to 10 min by regulating the flow rate of the acid catalyst containing aqueous solution to 113 g/h and the propylene flow rate to 26.5 g/h. In this reaction, the STY was 2,930 g/g-cat·h.

Example 4

The procedure of Example 1 was repeated except that the temperature was 350° C. and the molar ratio of water to propylene was set to 10 and the residence time was set to 10 min by regulating the flow rate of the acid catalyst containing aqueous solution to 118 g/h and the propylene flow rate to 27.5 g/h. In this reaction, the STY was 4,590 g/g-cat·h.

Example 5

The procedure of Example 1 was repeated except that the temperature was 340° C. and the molar ratio of water to propylene was set to 10 and the residence time was set to 10 min by regulating the flow rate of the acid catalyst containing aqueous solution to 122 g/h and the propylene flow rate to 28.4 g/h. In this reaction, the STY was 6,390 g/g-cat·h.

Example 6

The procedure of Example 1 was repeated except that the temperature was 320° C. and the molar ratio of water to propylene was set to 10 and the residence time was set to 10 min by regulating the flow rate of the acid catalyst containing aqueous solution to 129 g/h and the propylene flow rate to 30.1 g/h. In this reaction, the STY was 10,300 g/g-cat·h.

Example 7

The procedure of Example 1 was repeated except that the temperature was 310° C. and the molar ratio of water to propylene was set to 10 and the residence time was set to 10 min by regulating the flow rate of the acid catalyst containing aqueous solution to 133 g/h and the propylene flow rate to 30.9 g/h. In this reaction, the STY was 11,800 g/g-cat·h.

Example 8

The procedure of Example 1 was repeated except that the temperature was 300° C. and the molar ratio of water to propylene was set to 10 and the residence time was set to 10 min by regulating the flow rate of the acid catalyst containing aqueous solution to 136 g/h and the propylene flow rate to 31.7 g/h. In this reaction, the STY was 10,700 g/g-cat·h.

Example 9

The procedure of Example 1 was repeated except that the temperature was 280° C. and the molar ratio of water to propylene was set to 10 and the residence time was set to 10 min by regulating the flow rate of the acid catalyst containing aqueous solution to 142 g/h and the propylene flow rate to 33.2 g/h. In this reaction, the STY was 9,580 g/g-cat·h.

Example 10

The procedure of Example 1 was repeated except that the temperature was 260° C. and the molar ratio of water to propylene was set to 10 and the residence time was set to 10 min by regulating the flow rate of the acid catalyst containing aqueous solution to 149 g/h and the propylene flow rate to 34.7 g/h. In this reaction, the STY was 4,190 g/g-cat·h.

Example 11

The procedure of Example 1 was repeated except that the temperature was 250° C. and the molar ratio of water to propylene was set to 10 and the residence time was set to 10 min by regulating the flow rate of the acid catalyst containing aqueous solution to 152 g/h and the propylene flow rate to 35.4 g/h. In this reaction, the STY was 1,520 g/g-cat·h.

Example 12

The procedure of Example 1 was repeated except that the temperature was 380° C., the sulfuric acid concentration in the acid catalyst containing aqueous solution was regulated to 0.5 ppm (500 ppb) and the molar ratio of water to propylene was set to 10 and the residence time was set to 10 min by regulating the flow rate of the acid catalyst containing aqueous solution to 102 g/h, the propylene flow rate to 23.8 g/h and the volume of the reactor 25 to 50 mL. In this reaction, the STY was 172,000 g/g-cat·h.

Example 13

The procedure of Example 1 was repeated except that the temperature was 310° C., the sulfuric acid concentration in the acid catalyst containing aqueous solution was regulated to 500 ppm and the molar ratio of water to propylene was set to 10 and the residence time was set to 10 min by regulating the flow rate of the acid catalyst containing aqueous solution to 133 g/h and the propylene flow rate to 30.9 g/h. In this reaction, the STY was 1,340 g/g-cat·h.

Comparative Example 1

The procedure of Example 1 was repeated except that the temperature was 190° C., the pressure was 30 MPa, the sulfuric acid concentration in the acid catalyst containing aqueous solution was regulated to 50 ppm and the molar ratio of water to propylene was set to 10 and the residence time was set to 10 min by regulating the flow rate of the acid catalyst containing aqueous solution to 104 g/h and the propylene flow rate to 65.1 g/h. In this reaction, the STY was 0 g/g·cat·h.

Comparative Example 2

The procedure of Example 1 was repeated except that the temperature was 250° C., the pressure was 30 MPa, the sulfuric acid concentration in the acid catalyst containing aqueous solution was regulated to 0.0005 ppm (0.5 ppb) and the molar ratio of water to propylene was set to 10 and the residence time was set to 10 min by regulating the flow rate of the acid catalyst containing aqueous solution to 152 g/h and the propylene flow rate to 35.4 g/h. In this reaction, the STY was 0 g/g·cat·h.

Comparative Example 3

The procedure of Example 1 was repeated except that the temperature was 250° C., the pressure was 30 MPa, the sulfuric acid concentration in the acid catalyst containing aqueous solution was regulated to 50 ppm, and the molar ratio of water to propylene was set to 0.8 and the residence time was set to 10 min by regulating the flow rate of the acid catalyst containing aqueous solution to 27.8 g/h and the propylene flow rate to 81.1 g/h. In this reaction, the STY was 0 g/g·cat·h.

The reaction conditions and the STY values in Examples 1 to 13 and Comparative Examples 1 to 3 are shown in Table 1.

Comparative Example 4

The procedure of Example 1 was repeated except that the temperature was 380° C., the pressure was 30 MPa, and the molar ratio of water to propylene was set to 10 and the residence time was set to 10 min by regulating the flow rate of water to 102 g/h and the propylene flow rate to 23.8 g/h, and the acid catalyst was not used.

As a result, the STY value was not determined because the catalyst amount was 0. In Comparative Example 4, the selectivity of IPA was 3.6% and was a largely decreased value as compared with the selectivity of IPA of 59% in Example 1.

| | |
|---|---|
| 2-ethylhexylester acrylate | 55.0% |
| Methoxyethyl acrylate | 26.0% |
| Vinyl acetate | 14.7% |
| Azobisisobutylonitrile | 0.3% |
| felbinac | 4.0% |

As is clear from the results in Table 1, in each of Examples 1 to 13 satisfying the reaction conditions specified in the present invention, as the STY value of the hydration reaction is large, it is found that the reaction is advanced efficiently. On the other hand, of the conditions specified in the present invention, the temperature condition does not satisfy the specified conditions in Comparative Example 1, the sulfuric acid concentration condition does not satisfy them in Comparative Example 2 and the water/propylene molar ratio condition does not satisfy them in Comparative Example 3. In any of Comparative Examples 1 to 3, it is clear that hydration reaction is not advanced.

DESCRIPTION OF MARKS

Figure 1:
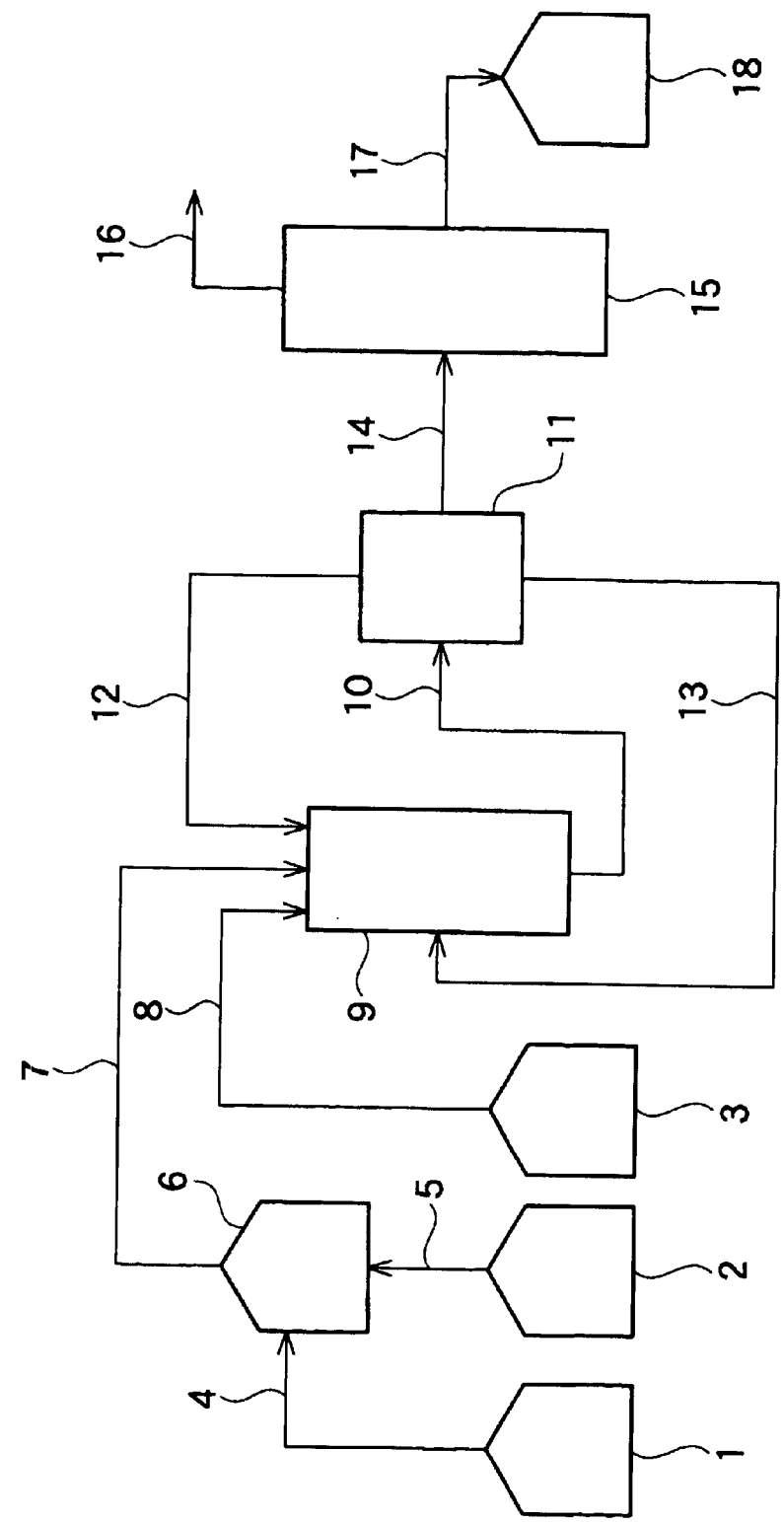
FIG. 1 is a flow sheet for carrying out the present invention.
Figure 2:
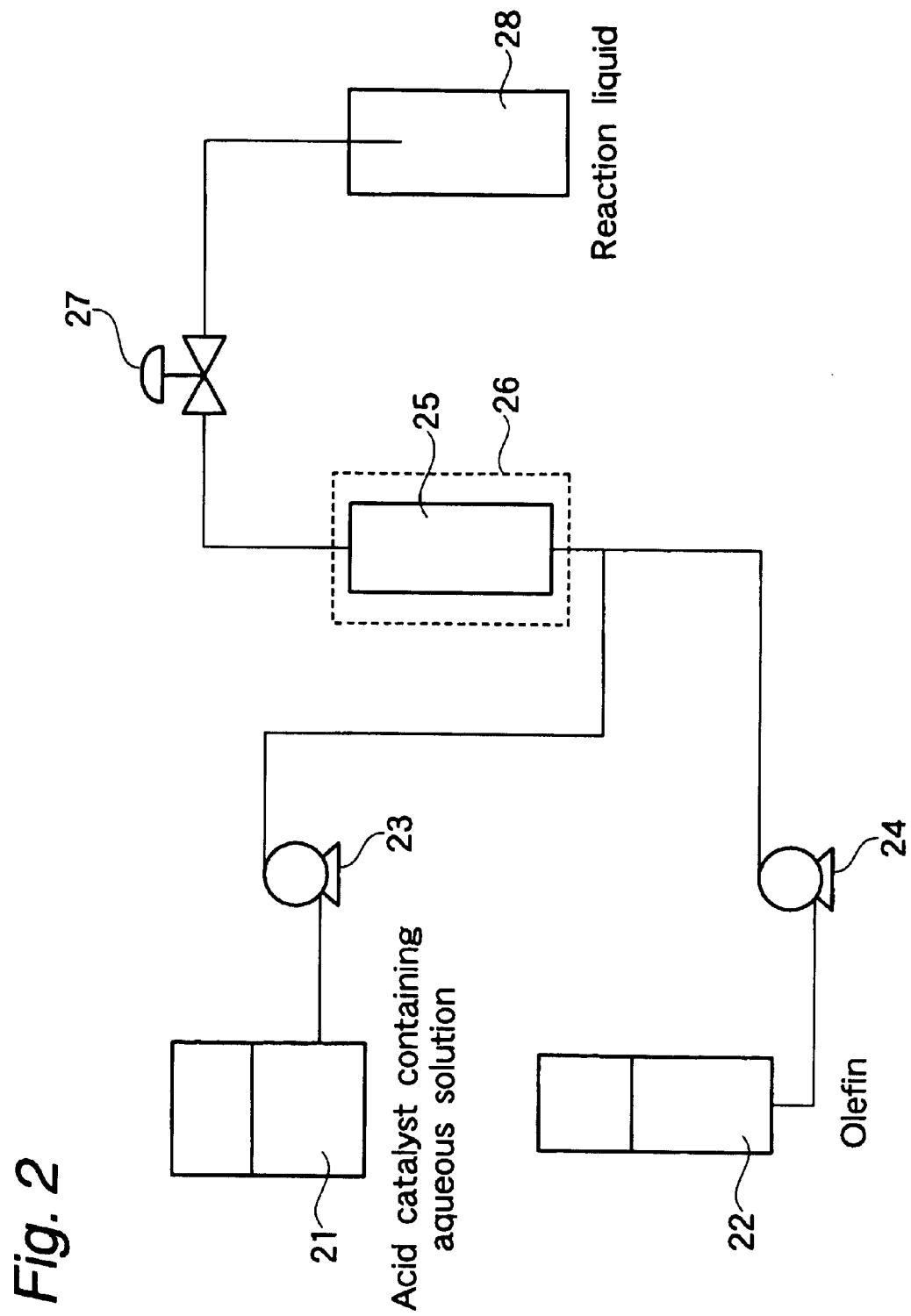
FIG. 2 is a schematic flow sheet for an apparatus used in Examples and Comparative Examples.

1 . . . tank for raw material water
2 . . . tank for acid catalyst
3 . . . tank for olefin raw material
4 . . . line for feeding water
5 . . . line for feeding acid catalyst
6 . . . tank for preparing acid catalyst containing aqueous solution
7 . . . line for feeding acid catalyst containing aqueous solution
8 . . . olefin feeding line
9 . . . reactor
10 . . . line for transporting reaction liquid
11 . . . separation process
12 . . . line for recovering and circulating unreacted olefin
13 . . . line for circulating acid catalyst containing aqueous solution
14 . . . line for transporting crude alcohol
15 . . . purification process
16 . . . line for discharging byproducts
17 . . . line for transporting production alcohol
18 . . . tank for production alcohol
21 . . . tank for acid catalyst containing aqueous solution
22 . . . tank for olefin raw material
23 . . . pump for feeding acid catalyst containing aqueous solution
24 . . . pump for feeding olefin
25 . . . reactor
26 . . . heater
27 . . . back pressure control valve
28 . . . reaction liquid tank

What is claimed is:

1. A process for producing a hydroxyl group containing compound which process comprises allowing an acid catalyst containing aqueous solution having an acid catalyst concentration of 1 ppb to 500 ppm to react with an aliphatic double bond having compound in a molar ratio (water/aliphatic double bond having compound) of water to aliphatic double bond having compound of from 1 to 50, at a reaction temperature of from 200 to 600° C. under a reaction pressure of from 1 to 100 MPa and thereby conducting hydration reaction of the aliphatic double bond containing compound with water.

2. The process for producing a hydroxyl group-containing compound according to claim 1 wherein the acid catalyst containing aqueous solution has an acid catalyst concentration of from 1 ppb to 300 ppm.

3. The process for producing a hydroxyl group containing compound according to claim 1 wherein the molar ratio (water/aliphatic double bond having compound) of water to the aliphatic double bond having compound is from 2 to 25.

4. The process for producing a hydroxyl group-containing compound according to claim 1 wherein the acid catalyst containing aqueous solution has an acid catalyst concentration of from 1 ppb to 70 ppm and the molar ratio (water/aliphatic double bond having compound) of water to the aliphatic double bond having compound is from 2 to 25.

5. The process for producing a hydroxyl group containing compound according to claim 1 wherein the reaction temperature is from 250 to 450° C. and the reaction pressure is from 4 to 90 MPa.

6. The process for producing a hydroxyl group containing compound according to any one of claims 1 to 4 wherein the acid catalyst is any one of hydrochloric acid, hydrogen chloride, chlorous acid, hypochlorous acid, sulfuric acid, sulfurous acid, nitric acid, nitrous acid, hydrogen fluoride, hydrofluoric acid, hydrogen bromide, hydrobromic acid, hydrogen iodide, hydriodic acid, orthophosphoric acid, metaphosphoric acid, phosphinic acid, phosphonic acid, diphosphoric acid, tripolyphosphoric acid, boric acid, silicotungstic acid, sodium silicotungstate, phosphotungstic acid, sodium phosphotungstate, silicomolybdic acid, sodium silicomolybdate, phosphomolybdic acid, sodium phosphomolybdate, benzoic acid, acetic acid, salicylic acid, oxalic acid, trifluoromethane sulfonic acid, p-toluenesulfonic acid and phenol.

7. The process for producing a hydroxyl group-containing compound according to any of claims 1 to 4 wherein the acid catalyst is any one of hydrochloric acid, sulfuric acid, nitric acid, orthophosphoric acid and metaphosphoric acid.

8. The process for producing a hydroxyl group-containing compound according to any one of claims 1 to 4 wherein the aliphatic double bond having compound is a monoolefin or diolefin.

9. The process for producing a hydroxyl group-containing compound according to any one of claims 1 to 4 wherein the aliphatic double bond having compound comprises at least one selected from ethylene, propylene, 1-butene, 2-butene, isobutene, 1-pentene, 2-pentene, isopentene, 1-hexene, 2-hexene, 3-hexene, isohexene, heptene, octene, nonene, decene, dodecene, cyclohexene, 1,3-butadiene, 1,3-pentadiene, 1,4-pentadiene, 1,3-hexadiene, 1,4-hexadiene, 1,5-hexadiene, 2,4-hexadiene, 1,6-heptadiene, 1,7-octadiene, 1,8-nonadiene, 1,9-decadiene, 1,3-cyclohexadiene, 1,4-cyclohexadiene, styrene, allyl benzene, trans-stilbene, cis-stilbene, triphenylethene, tetraphenyl ethene and divinyl benzene.

* * * * *